(12) United States Patent　(10) Patent No.: US 7,361,019 B2
Autran et al.　(45) Date of Patent: Apr. 22, 2008

(54) DENTAL INSTRUMENT

(75) Inventors: Domingo V. Autran, Bay City, MI (US); Dominic F. Verderese, Linwood, MI (US); Hector Daniel Herrera, Ft. Lauderdale, FL (US)

(73) Assignee: 3 D Interprizes, Inc, Bay City, MI (US)

( * ) Notice: Subject to any disclaimer, the term of this patent is extended or adjusted under 35 U.S.C. 154(b) by 0 days.

(21) Appl. No.: 11/294,052

(22) Filed: Dec. 5, 2005

(65) Prior Publication Data

US 2007/0128578 A1　Jun. 7, 2007

(51) Int. Cl.
*A61C 19/04*　(2006.01)
(52) U.S. Cl. .......................................... 433/72; 33/513
(58) Field of Classification Search ................ 433/72, 433/73, 75, 68, 69; 33/513, 514
See application file for complete search history.

(56) References Cited

U.S. PATENT DOCUMENTS

| | | | |
|---|---|---|---|
| 833,204 A * | 10/1906 | Crawford ..................... 433/72 |
| 1,649,664 A | 11/1927 | Carter | |
| 1,662,670 A * | 3/1928 | Harter ......................... 33/514 |
| 1,738,143 A * | 12/1929 | Hickok ........................ 433/72 |
| 1,804,567 A | 5/1931 | Pray | |
| 1,901,724 A * | 3/1933 | Bennett ....................... 33/513 |
| 1,907,923 A | 5/1933 | Willis | |
| 1,944,601 A * | 1/1934 | Gulick ........................ 33/513 |
| 2,048,989 A * | 7/1936 | Baribeau ..................... 33/513 |
| 2,125,809 A * | 8/1938 | Puckett ....................... 433/72 |
| 2,154,148 A | 4/1939 | Butts | |
| 2,832,137 A * | 4/1958 | Moore et al. ................. 433/73 |
| 4,843,720 A | 7/1989 | Kim | |
| 5,810,586 A | 9/1998 | Fjelstad | |
| 5,971,756 A | 10/1999 | Fjelstad | |
| 6,582,931 B1 | 6/2003 | Kois et al. | |

* cited by examiner

*Primary Examiner*—John J Wilson
(74) *Attorney, Agent, or Firm*—John K. McCulloch

(57) ABSTRACT

An instrument for determining the occlusal space between a person's upper and lower teeth thereby facilitating the formation of apparatus such as dentures and splints for removable positioning in the person's mouth.

5 Claims, 1 Drawing Sheet

DENTAL INSTRUMENT

This invention relates to a dental instrument especially adapted for use in enabling a dentist or denturist to produce properly fitting dentures or appliances for a patient.

BACKGROUND OF THE INVENTION

In the production of dentures and appliances such as occusal splints, it is necessary to provide for occlusal free space between the maxillary and mandibular arches. The free space occurs when a patient's jaws are unclenched and occupy a relaxed or at rest position in which the upper and lower teeth are vertically spaced from one another. The extent of the spacing or free space between the teeth is difficult to ascertain due to the inability of the dentist to obtain accurate measurements within the patient's mouth.

The problems associated with determining the occlusal free space when a patient's jaws are in a relaxed condition has been recognized heretofore and many proposals have been advanced for overcoming or minimizing such problems. However, not all of the proposals have been satisfactory for a variety of reasons, such as complexity, difficulty in use, and causing apprehension on the part of the patient.

An object of this invention is to provide an instrument for accurately determining the normal free space between a patient's upper and lower jaws and which overcomes the objectionable characteristics of previously proposed apparatus for similar purposes.

SUMMARY OF THE INVENTION

An instrument adapted for use in determining the free or at rest space between the upper and lower jaws of a patient and constructed in accordance with the invention comprises a pair of support arms having adjacent ends pivoted to one another for rocking movement about a substantially horizontal axis when the instrument is in use. One of the support arms is adapted for removable fitting to a patient's chin so as to enable the instrument to move vertically with the patient's lower jaw. The other support arm carries at its other end a coupling flange in which is adjustably mounted an indicator rod that is reciprocable so as to move toward and away from the patient's nose. The rod has at one end thereof a fitting or tip adapted to engage the nasal septum of the patient under certain conditions. Following appropriate orientation of the instrument with respect to the patient's chin and nose it may be used to determine the occlusal spacing between the patient's upper and lower teeth, thereby facilitating greatly the formation of a model of the patient's teeth as a preliminary step in the production of dentures or occlusal splints.

One of the distinct advantages of an instrument constructed in accordance with the invention is that it makes possible the accurate determination of the at rest position of a patient's jaws without having to make any measurements at all.

THE DRAWINGS

An instrument constructed in accordance with the presently preferred embodiment of the invention is illustrated in the accompanying drawings wherein.

THE PREFERRED EMBODIMENT

Figure 1:
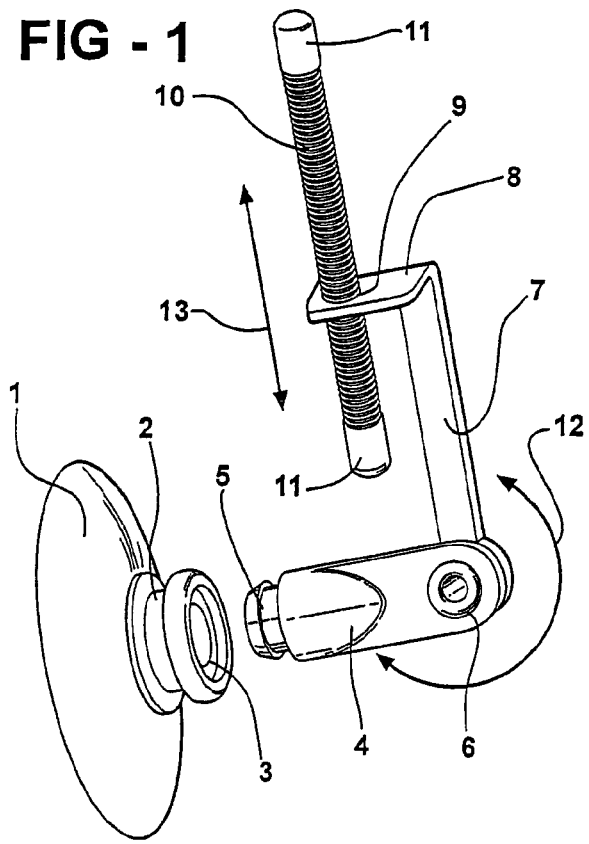
FIG. 1 is an exploded, isometric view of the instrument.
Figure 2:
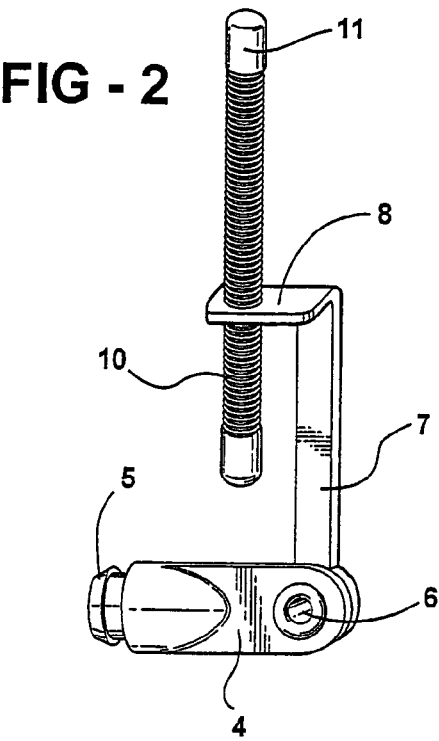
FIG. 2 is an isometric view of a portion of the apparatus shown in FIG. 1.
Figure 3:
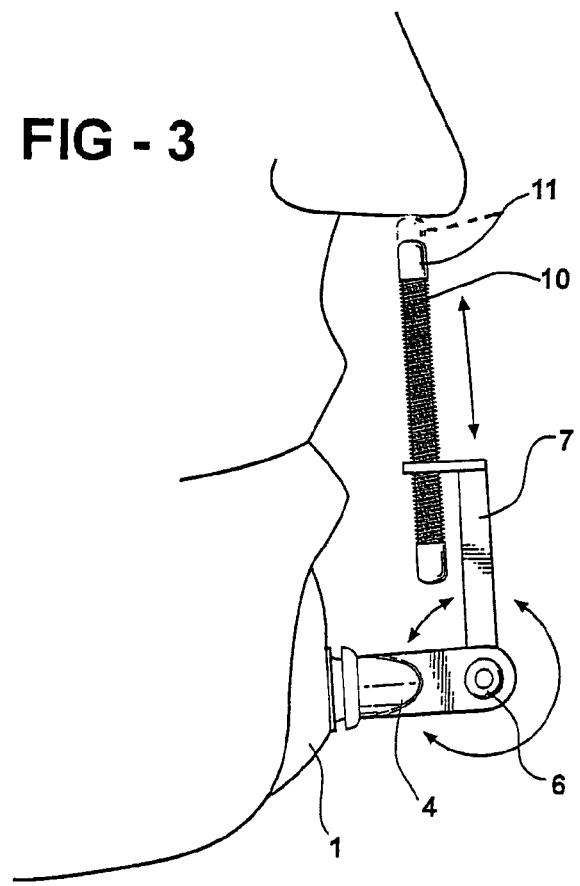
FIG. 3 is a side elevational view of the assembled apparatus mounted on a patient's chin.
Figure 4:
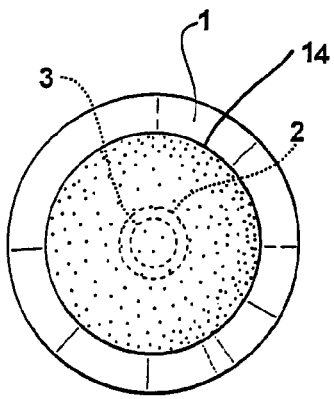
FIG. 4 is an enlarged elevational view of a chin mounting part of the apparatus.

Apparatus constructed in accordance with the preferred embodiment of the invention comprises a mounting suction cup 1 formed of pliable material. The cup 1 forms a socket adapted for removable attachment to a person's chin as indicated in FIG. 3. The interior surface of the cup which confronts the chin is concave so as to be more readily conformable to the configuration of the person's chin. Projecting from the opposite side of the cup is an integral, tubular extension 2 terminating in an annular, internal retaining flange 3.

A first support arm 4 terminates at one end in a circular coupling having at its free end an annular retainer 5 which is adapted to be accommodated in the extension 2. When assembling the parts 1 and 4 the retainer 5 passes beyond the flange 3 and is removably coupled to the suction cup 1 for rotation relative thereto about the longitudinal axis of the arm 4.

The opposite end of the support arm 4 is pivoted, as at 6, to one end of a second support arm 7 which terminates at its opposite end in a laterally extending coupling flange 8 provided with a threaded opening 9. Threadedly accommodated in the opening 9 is an elongate, correspondingly threaded indicator rod 10 terminating at its opposite ends in corresponding tips or fittings 11.

The arrangement of the support arms 4 and 7 is such that the arm 7 is rockable about the horizontal axis of the pivot 6 through at least 180° in the directions of the two headed arrow 12. The arrangement of the rod 10 is such that it is reciprocable axially, i.e. longitudinally, as indicated by the two headed arrow 13.

The mounting cup 1 is adapted to accommodate a removable attaching pad 14 having pressure sensitive adhesive on each of its opposite faces so as to enable it to be adhered removably to the inner surface of the suction cup 1 and to the chin of a person.

As has been indicated heretofore the instrument is especially adapted for use in preparing models of dentures or splints to fit a particular patient. In doing so it is essential to ascertain the extent of movement of the jaws of the patient between a normal at rest position and a clenched position. These two positions may be determined quickly and easily by use of the instrument disclosed herein.

To condition the instrument for use on a patient, the patient first is positioned in an upright, sitting position. The patient's chin is cleaned with a conventional alcohol cleaning preparation. The suction cup is moved toward engagement with the patient's chin following which the support arms 4 and 7 are adjusted in such manner as to enable one of the tips 11 to occupy a position below the patient's nose and in alignment with the nasal septum. The protective cover then may be removed from its overlying position with the pad 14, to expose the adhesive, following which the suction cup 1 is moved toward and into engagement with the patient's chin where it will be retained by the adhesive on the pad 14.

The patient then should move his lower jaw in a direction to clench the upper and lower jaws in the manner that occurs when the upper and lower teeth are in engagement. The rod 10 then is rotated in such direction as to move linearly a distance to cause the adjacent tip 11 to touch the nasal septum. The patient then should move his lower jaw away from the upper jaw to the patient's normal at rest position. This will create a space between the nasal septum and the tip 11, and such space corresponds to the free space between the person's jaws when they are in their at rest position. While the patient's jaws are in the at rest position, the rod may be moved upwardly to a position in which the adjacent tip 11 once again engages the nasal septum.

At this point the support arm 7, or the support arm 4, or both, can be rocked to positions in which the support arm 7 and the rod 10 permit access to the patient's mouth so that the dentist may utilize any conventional apparatus and methods to register the patient's bite. These methods may include the use of devices such as wax rims, bite blocks, impression material, or the like. Following placement of the appropriate device in the patient's mouth, the support arms 4 and 7 may be returned to the positions they occupy when the tip 11 confronts and bears upon the nasal septum. This will reflect the rest position of the patient's jaws, whereupon the splint or denture model material may be conformed to the patient's jaws while they are in their at rest position. This will preclude the possibility of over closing or under closing of the jaws.

Following the formation of the model for the dental appliance or dentures, the suction cup may be removed from the patient's chin, thereby enabling the instrument to be removed to a position clear of the patient.

Among the desirable characteristics of the instrument is its ability to accommodate protrusive and lateral movements of the lower jaw, adapt to patients of considerably different size, and still perform its function without modification. For example, in the arrangement of the parts as illustrated in FIG. 3, there is sufficient clearance between the plane of the patient's chin and the indicator rod 10 to enable the latter to occupy a position between the patient's face and the support arm 7. However, in a case where such space is more limited, the support arm 4 may be rotated about its longitudinal axis through 180° from the position shown in FIG. 3, following which the support arm 7 may be rotated upwardly through 180°, thereby positioning the support arm 7 between the rod 10 and the patient's face. These movements of the arms 4 and 7 enable the rod 10 to occupy a position that is more forwardly spaced from the patient's face than it is in the position shown in FIG. 3. Nevertheless, when the instrument is in its adjusted position, its operation is identical to that described earlier.

The disclosed embodiment is representative of a presently preferred form of the invention, but is intended to be illustrative rather than definitive thereof. The invention is defined in the claims.

We claim:

1. A dental instrument for use in determining the height of free space between upper and lower jaws of a person, said instrument comprising a first support arm having opposite ends; a second support arm having opposite ends; means rockably connecting one end of one of said support arms to one end of the other of said support arms for relative rocking movements of said support arms about a first axis; mounting means carried by one of said support arms at the opposite end thereof for mounting said instrument on a person's chin; an indicator member comprising an elongate rod; and means coupling said indicator member to the other of said support arms for axial movements of said indicator member relative to said second support arm in opposite directions toward and away from said person's nose when said instrument is mounted on said person's chin, said indicator member being capable of movement through a distance at least as great as that of said free space.

2. The instrument according to claim 1 wherein said mounting means includes an attaching member removably attachable to said person's chin, and means coupling said attaching member to said one of said support arms for rocking movements about a second axis independent of said first axis.

3. The instrument according to claim 2 wherein said attaching member comprises a suction cup.

4. The instrument according to claim 1 wherein said elongate rod of said indicator member is threaded and has a longitudinal axis, said rod being rotatable about said longitudinal axis.

5. A dental instrument for use in determining the height of free space between upper and lower jaws of a person, said instrument comprising a first support arm having opposite ends; a second support arm having opposite ends; means rockably connecting one end of one of said support arms to one end of the other of said support arms for relative rocking movements of said support arms about a first axis; mounting means carried by one of said support arms at the opposite end thereof for mounting said instrument on a person's chin; an indicator member; and means coupling said indicator member to the other of said support arms for movement relative to said support arm in directions toward and away from said person's nose when said instrument is mounted on said person's chin, said indicator member comprising an elongate rod axially movable in opposite directions, said mounting means including an attaching member removably attachable to said person's chin, and means coupling said attaching member to said one of said support arms for rocking movements about a second axis independent of said first axis, said attaching member comprising a suction cup.

* * * * *